United States Patent
Bernfield et al.

(10) Patent No.: US 6,284,729 B1
(45) Date of Patent: Sep. 4, 2001

(54) METHODS AND REAGENTS FOR REGULATING OBESITY

(75) Inventors: Merton Bernfield, Boston; Ofer Reizes, Newton, both of MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

(21) Appl. No.: 09/073,623

(22) Filed: May 6, 1998

Related U.S. Application Data (63) Continuation of application No. 08/965,356, filed on Nov. 6, 1997.
(60) Provisional application No. 60/030,758, filed on Nov. 6, 1996.

(51) Int. Cl.$^7$ ..................................................... A61K 38/00
(52) U.S. Cl. ................................................................ 514/12
(58) Field of Search ............................................... 514/12

(56) References Cited

U.S. PATENT DOCUMENTS

| | | |
|---|---|---|
| 3,625,214 | 12/1971 | Higuchi . |
| 4,244,946 | 1/1981 | Rivier et al. . |
| 4,305,872 | 12/1981 | Johnston et al. . |
| 4,316,891 | 2/1982 | Guillemin et al. . |
| 4,629,784 | 12/1986 | Stammer . |
| 4,789,734 | 12/1988 | Pierschbacher . |
| 4,792,525 | 12/1988 | Ruoslahti et al. . |
| 4,906,474 | 3/1990 | Langer et al. . |
| 4,925,673 | 5/1990 | Steiner et al. . |
| 5,486,599 | 1/1996 | Saunders et al. . |
| 5,766,877 * | 6/1998 | Stark et al. . |
| 5,843,652 * | 12/1998 | Woychik . |
| 5,908,906 | 6/1999 | Lee et al. . |

FOREIGN PATENT DOCUMENTS

| | | |
|---|---|---|
| WO 93/01286 A2 | 1/1993 | (WO) . |
| WO 95/00633 A2 | 1/1995 | (WO) . |
| WO 95/34316 A1 | 12/1995 | (WO) . |
| WO 97/47316 A1 | 12/1997 | (WO) . |

OTHER PUBLICATIONS

Agrawal, et al., "Oligodeoxynucleoside phosphoramidates and phosphorothioates as inhibitors of human immunodeficiency virus," *Proc. Natl. Acad. Sci. USA* 85(19):7079–7083 (1988).

Askew, et al., "Molecular Recognition with Convergent Functional Groups. 6. Synthetic and Structural Studies with a Model Receptor for Nucleic Acid Components," *J. Am. Chem. Soc.* 111(3):1082–1090 (1989).

Bernfield, et al., "Biology of the Syndecans: A Family of Transmembrane Heparan Sulfate Proteoglycans," in *Annu. Rev. Cell Biol.*, (Palade, et al., eds.) 8:365–393 (Annual Reviews Inc., Palo Alto, CA, 1992).

Clackson, et al., "Making antibody fragments using phage display libraries," *Nature* 352(6336):624–688 (1991).

Colditz, "Economic costs of obesity," *Am. J. Clin. Nutr.* 55(2):503S–507S (1992).

Daugherty, et al., "Polymerase chain reaction facilitates the cloning, CDR–grafting, and rapid expression of a murine monoclonal antibody directed against the CD18 component of leukocyte integrins," *Nucl. Acids Res.* 19(9):2471–2476 (1991).

David, "Integral membrane heparan sulfate proteoglycans," *FASEB J.* 7(11):1023–1030 (1993).

David, et al., "Molecular Cloning of a Phosphatidylinositol–anchored Membrane Heparan Sulfate Proteoglycan from Human Lung Fibroblasts," *J. Cell Biol.* 111(6):3165–3176 (1990).

Elenius, et al., "Induced Expression of Syndecan in Healing Wounds," *J. Cell Biol.* 114(3):585–595 (1991).

Ellington, et al., "Selection in vitro of single–stranded DNA molecules that fold into specific ligand–binding structures," *Nature* 355(6363):850–852 (1992).

Ezzell, "Fat Times for Obesity Research: Tons of New Information, but How Does It All Fit Together," *J. NIH Res.* 7:39–43 (1995).

(List continued on next page.)

Primary Examiner—William R. A. Jarvis
(74) Attorney, Agent, or Firm—Holand & Knight LLP (57) ABSTRACT

It has now been demonstrated that syndecan binds to and interacts with MC4-R, and thereby modulates neuropeptide regulation of body weight, via the agouti/MC4-R signaling pathway. Transgenic animals were made initially using a construct including a cytomegalovirus promoter and the 3' untranslated region, including the polyadenylation site, of the bovine growth hormone gene, as well as cDNA encoding syndecan-1. The mice express the syndecan-1 transgene in many tissues, with expression in the brain occurring preferentially in their hypothalamus. These mice are characterized by elevated levels of circulating syndecan-1 ectodomain and exhibit enormous weight gain after reaching sexual maturity, but have a relatively normal distribution of fat, are completely healthy and heterozygotes reproduce, and show other indicators associated with obesity in humans. Agouti mice which are transgenic for syndecan-1 ectodomain demonstrate that syndecan-1 and agouti interact, potentiating obesity. The double heterozygote shows both an earlier onset, and greater extent, of obesity than either normal agouti or the original transgenic syndecan-1 mice.

Based on these studies and animal models, one can design and test compounds regulating obesity. These mice are also useful in understanding the factors involved in weight regulation and in designing and screening for drugs which are involved in weight regulation and that can either enhance or reduce appetite and activity.

12 Claims, 3 Drawing Sheets

OTHER PUBLICATIONS

Flier, "Commentary—Leptin expression and action: New experimental paradigms," *Proc. Natl. Acad. Sci. USA* 94(9):4242–4245 (1997).

Greenway, "Surgery of Obesity," *Endo. Metab. Clin. N. Amer.* 25(4):1005–1027 (1996).

Gregoriadis, "Liposomes," Chapter 14, Drug Carriers in Biology and Medicine pp. 287–341 (Academic Press, 1979).

Guan, et al., "Fibronectin/integrin interaction induces tyrosine phosphorylation of a 120–kDa protein," *Cell Reg.* 2(11):951–964 (1991).

Gura, "Obesity Sheds Its Secrets," *Science* 275:752–753 (1997).

Harada, et al., "Monoclonal antibody G6K 12 specific for membrane–associated differentiation marker of human stratified squamous epithelia and squamous cell carcinoma," *J. Oral Pathol. Med.* (Denmark), 22(f):145–152 (1993).

Hayashi, et al., "Immunocytochemistry of Cell Surface Heparan Sulfate Proteoglycan in Mouse Tissues. A Light and Electron Microscopic Study," *J. Histochem. Cytochem.* 35(10):1079–1088 (1987).

Higashiyama, et al., "Heparin–binding EGF–like Growth Factor Stimulation of Smooth scle Cell Migration: Dependence on Interactions with Cell Surface Heparan Sulfate," *J. Cell Bio.* 122(4):933–940 (1993).

Huszar, et al., "Targeted Disruption of the Melanocortin–4–Receptor Results in Obesity in Mice," *Cell* 88(1):131–141 (1997).

Inai, et al., "Immunohistochemical detection of an enamel protein–related epitope in rat bone at an early stage of osteogenesis," *Histochemistry* (German), 99(5):335–362 (1993).

Itakura, et al., "Synthesis and Use of Synthetic Oligonucleotides," *Ann. Rev. Biochem.* 53:323–356 (1984).

Joyner, et al., "Production of a mutation in mouse En–2 gene by homologous recombination in embryonic stem cells," *Nature* 338(6211):153–156 (1989).

Kabat, et al., Sequences of Proteins of Immunological Interest, 4th Ed. (U.S. Dept. Health and Human Services, Bethesda, MD, 1987).

Lee, et al., "Change in Body Weight and Longevity," *JAMA* 268(15):2045–2049 (1992).

Lewis, et al., "Automated site–directed drug design: the concept of spacer skeletons for primary structure generation," *Proc. R. Soc. Lond.* 236:125–140 and 141–162 (1989).

Long, et al., "Weight Loss in Severely Obese Subjects Prevents the Progression of Impaired Glucose Tolerance to Type II Diabetes," *Diabetes Care* 17(15):372–375 (1994).

McKinaly, et al., "Rational Design of Antiviral Agents," *Annu. Rev. Pharmacol. Toxicol.* 29:111–122 (1989).

Merrifield, "Solid Phase Peptide Synthesis. I. The Synthesis of a Tetrapeptide," *J. Am. Chem. Soc.* 85:2149–2154 (1964).

Mortimer, et al., "Use of Gene–Manipulated Models To Study The Physiology Of Lipid Transport," *Clinical and Experimental Pharmacology and Physiology* 24(3/4):281–285 (1997).

Mulder, et al., "Characterization of Two Human Monoclonal Antibodies Reactive with HLA–B12 and HLA–B60, Respectively, Raised by in vitro Secondary Immunization of Peripheral Blood Lymphocytes," *Hum. Immunol.* 36(3):186–192 (1993).

Narang, et al., "Chemical Synthesis of Deoxyoligonucleotides by the Modified Triester Method," *Methods Enzymol.* 65:610–620 (1980).

National Task Force on Obesity, "Long–term Pharmacotherapy in the Management of Obesity," *JAMA* 276(23):1907–1915 (1996).

NIH Conference, "Gastrointestinal Surgery for Severe Obesity," *Ann Intern Med.* 115(12):956–961 (1991).

NIH Technology Assessment Conference Panel, "Methods for Voluntary Weight Loss and Control," *Ann. Intern. Med.* 119(7):764–770 (1993).

Offensperger, et al., "In Vivo inhibition of duck hepatitis B virus replication and gene expression by phosphorothioate modified antisense oligodeoxynucleotides," *EMBO J.* 12(3):1257–1262 (1993).

Ollmann, et al., "Antagonism of central melancortin receptors in vitro and in vivo by agouti–related protein," *Science* 278, 135–138 (1997).

Paulson, et al., "Glycosyltransferases," *J. Biol. Chem.* 264(30):17615–17618 (1989).

Perry, et al., *QSAR: Quantitative Structure–Activity Relationships in Drug Design* (Fauchère, ed.), pp. 189–193 (Alan R. Liss, inc. 1989).

Potter, et al., "Enhancer–dependent expression of human κ immunoglobulin genes introduced into mouse pre–B lymphocytes by electroporation," *Proc. Natl. Acad. Sci. USA* 81(22):7161–7165 (1984).

Rapraeger, "The coordinated regulation of heparan sulfate, syndecans and cell behavior," *Curr. Opin. Cell Biol.* 5(5):844–853 (1993).

Ripka, "Computers Picture the Perfect Drug," *New Scientist* 1617:54–57 (1988).

Rouvinen, et al., "Computer–Aided Drug Design," *Acta Pharmaceutica Fennica* 97:159–166 (1988).

Ruoslahti, et al., "Proteoglycans as Modulators of Growth Factor Activities," *Cell* 64(5):867–869 (1991).

Sarin, et al., "Inhibition of acquired immunodificiency syndrome virus by oligodeoxynucleoside methylphosphonates," *Proc. Natl. Acad. Sci. USA* 85(20):7448–7794 (1989).

Shaw, et al., "Modified deoxyoligonucleotides stable to exonuclease degradation in serum," *Nucleic Acids Res.* 19(4):747–750 (1991).

Southern, et al., "Transformation of Mammalian Cells to Antibiotic Resistance with a Bacterial Gene Under Control of the SV40 Early Region Promoter," *J. Mol. Appl. Gen.* 1(4):327–341 (1982).

Stäuber, et al., "Rapid generation of monoclonal antibody–secreting hybridomas against African horse sickness virus by in vitro immunization and the fusion/cloning technique," *J. Immunol. Methods* (Netherlands), 161(2):157–168 (1993).

Szostak, "in vitro genetics" *TIBS* 19:89, (1992).

Venkateswaran, et al., "Production of Anti–Fibroblast Growth Factor Receptor Monoclonal Antibodies by In Vitro Immunization," *Hybridoma* 11(6):729–739 (1992).

Wolf, et al., "The Cost of Obesity," *Pharmacoeconomics* 5(Supp. 1):34–37 (1994).

Woods, et al., "A Synthetic Peptide from the COOH–Terminal Heparin–binding Domain of Fibronectin Promotes Focal Adhesion Formation," *Molec. Biol. Cell* 4(6):605–613 (1993).

Yayon, et al., "Cell Surface, Heparin–like Molecules Are Required for Binding of Basic Fibroblast Growth Factor to Its High Affinity Receptor," *Cell* 64(4):841–848 (1991).

Yen, et al., "Obesity, diabetes, and neoplasia in yellow A9vy/–mice: ectopic expression of the agouti gene," *FASEB J.* 8, 479–488 (1994).

Zimmer, et al., "Production of chimaeric mice containing embryonic stem (ES) cells carrying a homoeobox Hox 1.1 allele mutated by homologous recombination," *Nature* 338(6211):150–153 (1989).

* cited by examiner

METHODS AND REAGENTS FOR REGULATING OBESITY

This application is a continuation of U.S. Ser. No. 08/965,356, filed Nov. 6, 1997, which claims priority to U.S. Ser. No. 60/030,758, filed Nov. 6, 1996, both entitled "Methods and Reagents for Regulating Obesity", by Merton Bernfield and Ofer Reizes.

The United States government has certain rights in this invention by virtue of National Institutes of Health grant Nos. RO1 HD06763-24, RO1 CA28735-15, UO1 HD28882-05 to Merton Bernfield, and F32 NS09649-02 to Ofer Reizes.

BACKGROUND OF THE INVENTION

Obesity is a well established risk factor for a number of potentially life-threatening diseases such as atherosclerosis, hypertension, diabetes, stroke, pulmonary embolism, and cancer. Furthermore, it complicates numerous chronic conditions such as respiratory diseases, osteoarthritis, osteoporosis, gall bladder disease, and dyslipidemias. The enormity of this problem is best reflected in the fact that death rates escalate with increasing body weight. More than 50% of all-cause mortality is attributable to obesity-related conditions once the body mass index (BMI) exceeds 30 $kg/m^2$, as seen in 35 million Americans. (Lee1992. JAMA. 268:2045–2049). By contributing to greater than 300,000 deaths per year, obesity ranks second only to tobacco smoking as the most common cause of potentially preventable death. (McGinnis 1993 MA.270:2207–2212). Accompanying the devastating medical consequences of this problem is the severe financial burden placed on the health care system in the United States. The estimated economic impact of obesity and its associated illnesses from medical expenses and loss of income are reported to be in excess of $68 billion/year. (Colditz G. 1992. Am J Clin Nutr. 55:503S–507S). This does not include the greater than $30 billion per year spent on weight loss foods, products, and programs. (Wolf 1994. Pharmacoeconomics. 5:34–37).

A major reason for the long-term failure of established approaches is their basis on misconceptions and a poor understanding of the mechanisms of obesity. Conventional wisdom maintained that obesity is a self-inflicted disease of gluttony. Comprehensive treatment programs, therefore, focused on behavior modifications to reduce caloric intake and increase physical activity using a myriad of systems. These methods have limited efficacy and are associated with recidivism rates exceeding 95%. (NIH Technology Assessment Conference Panel. 1993. Ann Intern Med. 119:764–770). Failure of short-term approaches, together with the recent progress made in elucidating the pathophysiology of obesity, have lead to a reappraisal of pharmacotherapy as a potential long-term, adjuvant treatment. (National Task Force on Obesity. 1996. JAMA. 276:1907–1915). The premise is that body weight is a physiologically controlled parameter similar to blood pressure and obesity is a chronic disease similar to hypertension. The goal of long-term (perhaps life long) medical therapy would be to facilitate both weight loss and subsequent weight maintenance in conjunction with a healthy diet and exercise. To assess this approach, the long-term efficacy of currently available drugs must be judged against that of non-pharmacological interventions alone. Currently, no single drug regimen emerges as superior in either promoting or sustaining weight loss. Although promising, the success of this approach is limited by the efficacy of currently available anorexiant drugs. Surgical interventions, such as gastric partitioning procedures, jejunoileal bypass, and vagotomy, have also been developed to treat severe obesity. (Greenway 1996. Endo Metab Clin N Amer. 25:1005–1027). Although these procedures induce similar rates of early weight loss as nonsurgical interventions, they have been shown to maintain a weight loss of up to 33% for more than 10 years. (Long 1994. Diabetes Care. 17:372–375). While still far from optimal, this is a substantial improvement over that achieved with behavioral and medical management alone. The superior long-term outcome with surgical procedures in attributed to the inherent permanence of the intervention which addresses the chronic nature of the disease. Although advantageous in the long run, the acute risk benefit ratio has reserved these invasive procedures for morbidly obese patients according to the NIH consensus conference on obesity surgery (BMI>40 $kg/m^2$). (NIH Conference. 1991. Ann Intern Med. 115:956–961). Therefore, this is not an alternative for the majority of overweight patients unless and until they become profoundly obese and are suffering the attendant complications.

No one knows all of the mechanisms involved in regulation of weight gain, although it is believed that many genetic as well as environmental factors, including diet and exercise, play major, interrelated roles. A number of publications have reported the discovery of genes that have been "knocked out" or overexpressed in transgenic mice, resulting in affected animals becoming incredibly obese, or vice versa. See, for example, Ezzell, "Fat Times for Obesity Research: Tons of New Information, but How Does It All Fit Together" *J. NIH Res.* 7, 39–43 (October 1995). Researchers have reported the cloning of at least two distinct genes, Ob which encodes a protein "leptin" believed to cause weight reduction in obese animals, and Db, which is believed to cause weight gain in animals. Other genes which have been reported include the fat, tub, agouti, and melanocortin 4 receptor genes. Recent reviews relating to the insights regarding the mechanisms involved in obesity help to understand these complex pathways. See, for example, Trish Gura, *Science* 275, 752–753 (Feb. 7, 1997) and Jeffrey S. Flier, *Proc. Natl. Acad. Sci. USA* 94, 4242–4245 (April 1997). Leptin, discovered in 1994 by Jeffrey Friedman's team at Rockefeller University, NY, is a 16 kD protein produced by the obesity (ob) gene of mice. Homozygotes with defective ob genes are unable to reproduce, stay warm, or grow normally, and become grossly overweight. The receptor for leptin has now been identified and cloned. Defects in the receptor also result in grossly obese animals. The receptor is expressed in the brain primarily in four regions, including the arcuate nucleus. In humans, however, the linkage between obesity and overexpression of leptin does not seem to be closely correlated, and no individuals have been identified that have a mutated Ob receptor or gene. Another molecule which appears to be important in weight control is the appetite-stimulating neurotransmitter referred to as neuropeptide Y or "NPY". NPY levels are elevated in animals with decreased levels of leptin. Genetic studies with knockout NPY and ob/ob animals indicate that NPY plays a role in, but is not a controlling factor, in obesity. Another line of research has implicated a role in obesity for the melanocortin receptor ("MCR"). Two MCRs, MCR3 and MCR4, are produced in the arcuate nucleus of the hypothalamus, a prime target of leptin action as well as of NPY production. Synthetic peptides mimicking melanocortins which bind to MCR-4 suppress feeding. Animals in which the gene encoding MCR-4 has been knocked out show the opposite behavior, exhibiting high weight gain and high NPY expression.

The genetic studies have clarified, but not definitively determined, the factors which are responsible for obesity, nor provided compounds for treatment or prevention of obesity.

It is therefore an object of the present invention to provide another method and means for regulating obesity.

It is a further object of the present invention to provide a method and means for screening for drugs which can regulate weight gain, alone or in combination with other drugs.

It is a still further object of the present invention to provide a method and means for studying the role of hormones and development on weight control.

SUMMARY OF THE INVENTION

It has now been demonstrated that syndecan binds to and interacts with MC4-R, and thereby modulates neuropeptide regulation of body weight, via the agouti/MC4-R signaling pathway. Transgenic animals were made initially using a construct including a cytomegalovirus promoter and the 3' untranslated region, including the polyadenylation site, of the bovine growth hormone gene, as well as cDNA encoding syndecan-1. The mice express the syndecan-1 transgene in many tissues, with expression in the brain occurring preferentially in their hypothalamus. These mice are characterized by elevated levels of circulating syndecan-1 ectodomain and exhibit enormous weight gain after reaching sexual maturity, but have a relatively normal distribution of fat, are completely healthy and heterozygotes reproduce, and show other indicators associated with obesity in humans. Agouti mice which are transgenic for syndecan-1 ectodomain demonstrate that syndecan-1 and agouti interact, potentiating obesity. The double heterozygote shows both an earlier onset, and greater extent, of obesity than either normal agouti or the original transgenic syndecan-1 mice.

Based on these studies and animal models, one can design and test compounds regulating obesity. These mice are also useful in understanding the factors involved in weight regulation and in designing and screening for drugs which are involved in weight regulation and that can either enhance or reduce appetite and activity.

BRIEF DESCRIPTION OF THE DRAWINGS

FIG. 1b, plotting MC4-R activity as a function of syndecan-1 ectodomain concentration).

DETAILED DESCRIPTION OF THE INVENTION

Transgenic animals have been developed which are useful in screening for compounds and testing of compounds for the treatment of a wide range of eating disorders, including idiopathic obesity, anorexia nervosa, and cachexia due to disease. The latter is a significant clinical problem due to several cancers, cancer chemotherapy, chronic inflammatory diseases, rheumatoid and collagen diseases and chronic infections. Evidence accumulating over the past several years indicates that hormones, neuropeptides and neurotransmitters act on the hypothalamus to establish a "set point" that maintains a balance between feeding behavior and energy expenditure. A very small change in this set point can cause severe obesity or starvation. Expression of the syndecan-1 transgene in the hypothalamus appears to interfere with this set point mechanism. It is believed this occurs through interaction with the melanocortin-4 receptor (MC4R), which is known to be involved in weight regulation.

The cellular microenvironment contains many insoluble or immobilized as well as diffusible or circulating effector molecules that interact with cell surface receptors that signal cells to change behavior. Complex cellular behaviors such as those resulting in wound repair are influenced by a variety of soluble growth factors, cytokines, and insoluble extracellular matrix components. To exert their effects, many of these effector molecules must bind to the heparan sulfate chains that are at the surface of nearly all adherent cells (Ruoslahti and Yamaguchi, Cell, 64:867 (1991)). For example, interaction with cell surface heparan sulfate is required for cells to respond to the growth factors FGF-2 (Rapraeger, et al., Science, 252:1705 (1991); Yayon, et al. Cell, 64:841 (1991)) and HB-EGF (Higashiyama, et al., J. Cell Bio., 122:933–940 (1993)), and to the matrix component fibronectin (Guan, et al. Cell Reg., 2:951 (1991); Woods, et al., Molec. Biol. Cell, 4:605 (1993)). Indeed, Guan, et al. (1991); Bernfield, et al., in Annu. Rev. Cell Biol., G. E. Palade, B. M. Alberts, J. A. Spudich, Eds. (Annual Reviews Inc., Palo Alto, Calif., 1992), 8:365–393); Jalkanen, et al., Trends in Glyco-science and Glycotech, 5:107 (1993); G. David, FASEB J., 7:0123 (1993); and A. C. Rapraeger, Curr. Opin. Cell Biol., 5:844 (1993)) have proposed that cell surface heparan sulfate, which is derived mostly from the four members of the syndecan family of transmembrane proteoglycans (G. David, et al., J. Cell Biol., 111:3165 (1990)), acts together with specific signaling receptors to mediate the cellular response to such effectors. Changes in the abundance of cell surface heparan sulfate probably regulates the action of these effector molecules, yet it is not known how the amount of heparan sulfate at the cell surface is controlled.

Cell surface heparan sulfate mediates the activity of several growth factors, extracellular matrix components, proteases and other cellular effectors involved in wound repair. Syndecan-1, a major transmembrane heparan sulfate proteoglycan, is induced transiently on mesenchymal cells during the repair of skin wounds. Accordingly, induction of syndecan-1 can influence this process. Syndecan-1 induction can trigger cellular behaviors such as proliferation and migration that are involved in wound repair due to its ability to bind and thus augment the action of heparin-binding growth factors, including FGF-2, HB-EGF, and PDGF-AB, each found in repairing wounds. The expression of syndecan-1 is highly regulated in vivo. In mature tissues, syndecan-1 is expressed on the surface of epithelial cells but not on the surface of mesenchymal cells (K. Hayashi, et al., *J. Histochem. Cytochem.*, 35:1079 (1987)). However, during cutaneous wound repair in the mouse, syndecan-1 is lost from the surface of the epithelial cells migrating into the wound and is induced on the dermal endothelial cells and fibroblasts of the forming granulation tissue (K. Elenius, et al., *J. Cell Biol.*, 114:585 (1991)).

The syndecan core protein from mouse mammary epithelia was first cloned by Saunders, et al. 1989a). Other syndecans are also known and have now been cloned, including syndecan 2, 3 and 4. These syndecans constitute the syndecan family. They are characterized by a similar domain structure, highly conserved sequences, and a conserved exon organization in the genes studied to date. The molecular sizes of syndecan-1, -2, -3 and -4, are 311 amino acids, 384 amino acids, 201 amino acids, and 202 amino acids. Each protein contains a cluster of similar putative GAG attachment sites distal from the plasma membrane near the N-terminus of the mature protein: one site (or two in syndcan-3) is of the syndecan-type sequence and the other two (or three) sites are of the serglycin-type. Syndecan-1 and -3 contain putative GAG attachment sites that are absent in syndecan-2 and -4. The glycosaminoglycan (GAG) chains on the syndecans are critical to their functions. Variations in expression during development and by tissue, as well as the structure and composition, determine the role of the syndecans. However, little has been known other than in wound healing and cell-cell interaction until the studies described herein.

I. Development of a Model of Body Fat Regulation

Transgenic mice were originally developed from a single founder animal having a cDNA construct including a cytomegalovirus promoter and the 3' untranslated region, including the polyadenylation site, of the bovine growth hormone gene, as well as cDNA encoding syndecan-1. The detailed construction of this vector is described below, as are the pedigrees and results obtained with three distinct lines of animals, and additional lines containing the construct but with stop codons which prevent protein expression. A single founder was originally identified which generated two lines. Both syndecan-1 expressing lines show the same phenotype: shedding of syndecan-1 into the blood, overexpression of syndecan-1 in the hypothalamus, overeating behavior and obesity in mature animals. Their morphology is otherwise normal. One line is characterized by a single insert "A". A second line is characterized by the same construct inserted at a separate location "B". The founder animal had both inserts, which segregated upon breeding, as discussed below. As described in more detail in the tables, unlike normal non-transgenic littermates, the transgenic animals continue to gain weight following sexual maturity and cessation of linear growth, becoming markedly obese: homozygotes exceed twice normal weight at five months of age. The phenotype is dominant and is due to a defect in energy balance; food intake is excessive (double normal consumption), locomotor activity is reduced, fat pads, mammary glands, pancreas and liver are enlarged, carcass triglyceride is increased more than four-fold, and blood and urine glucose levels are elevated only in the overtly obese mice. Many organs overexpressed syndecan-1. In brain, both syndecan-1 proteoglycan (PG) and mRNA selectively localized to the paraventricular, arcuate, and lateral hypothalamic nuclei. In control lines (Syndecan-1 C, F and G), transgene mRNA is expressed in all tissues. In the hypothalamus, expression is observed in the arcuate, dorsomedial, lateral, suprachiasmatic, and supraoptic hypothalamic nuclei in a similar pattern in syndecan A, B and E lines.

A. Design and Construct of Syndecan-1 Construct.

The construct has two essential elements: (1) a promoter which localizes expression in the hypothalamus, especially in the paraventricular, arcuate, and lateral hypothalamic nuclei, and regulatory sequences required for processing of the transcript; (2) a nucleic acid molecule encoding a syndecan.

1. Promoters and Regulatory Sequences

Overexpression or preferential expression of the syndecan in the hypothalamus is believed to be an important aspect of the transgenic animals. This can be achieved using a promoter such as the truncated cytomegalovirus promoter which is sold by Invitrogen. Other neurotropic promoters, many of which are commercially available, may also be useful. Regulatory sequences required for processing of the transcript may also be included in the construct. A preferred example is the 3' untranslated region (UTR) of the bovine growth hormone gene, included in the Invitrogen vector, although any UTR can be used. It is believed the UTR stabilizes the transcript and may have an impact on localization.

2. Syndecan Encoding Sequences

Nucleic acids encoding syndecan can be expressed in animals using known methods and procedures. For this purpose, syndecan transgene constructs can be made using known vectors and transcription and translation control sequences, and known principles and techniques of recombinant DNA. DNA encoding syndecan-1, homologs of syndecans, derivatives of syndecans, and chimeric syndecans, all useful for making syndecan transgene constructs, are described in U.S. Pat. No. 5,486,599 to Saunders et al., which is hereby incorporated by reference.

3. Assembly of the Syndecan-1 Construct

A syndecan transgene construct was made using expression vector pcDNA3 (Invitrogen). This vector contains a portion of the cytomegalovirus intermediate/early promoter/enhancer and the 3' untranslated region, including the polyadenylation site, of the bovine growth hormone gene. Vector pcDNA3 was cut with HindIII and a cDNA fragment encoding syndecan-1 was inserted between the expression elements in pcDNA3. The syndecan-1 cDNA fragment was an 1183 bp HindIII fragment including the syndecan-1 coding region, 10 bp of the syndecan-1 5' untranslated region, and about 200 bp of the syndecan-1 3' untranslated region. The resulting plasmid contains a syndecan expression cassette of approximately 2500 bp MluI/DraIII fragment. The cassette includes about 600 bp of the cytomegalovirus (CMV) promoter, syndecan-1 cDNA sequence, and about 200 bp of the 3' untranslated region of the bovine growth hormone gene. Non-translatable constructs (syndecan C, F and G) were made by inserting three stop codons immediately following the signal peptide in the syndecan-1 cDNA. The nucleic acid sequences encoding the different syndecans, including syndecan-1, are available from GENEBANK.

B. Transgenic Animals.

The fragment encoding the syndecan was excised from the plasmid and injected into fertilized FVB mouse oocytes. The injected oocytes were introduced into FVB mice resulting in transgenic offspring.

Although the study described herein used mice, it would clearly be routine to apply the same technology to other rodents such as rats or hamsters, or even to larger animals such as sheep, pigs, or goats where there may be commercial advantages in animals that continue to eat and gain weight to a significant degree more than their normal counterparts. For screening of most drugs, however, mice would be preferred due to the small size and rapid rate of breeding. Transgenic animals can be made either by microinjection or by embryonic stem cell manipulation.

The methods for constructing transgenic animals are well known and are usually either microinjection, where a gene is inserted, or embryonic stem cell manipulation, where a gene is to be knocked out.

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats.

1. Microinjection Procedures

The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein. These techniques are readily applicable to embryos of other animal species, and, although the success rate is lower, it is considered to be a routine practice to those skilled in this art.

Female animals are induced to superovulate using methodology adapted from the standard techniques used with mice, that is, with an injection of pregnant mare serum gonadotrophin (PMSG; Sigma) followed 48 hours later by an injection of human chorionic gonadotrophin (hCG; Sigma). Females are placed with males immediately after hCG injection. Approximately one day after hCG, the mated females are sacrificed and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5þC incubator with a humidified atmosphere at 5% $CO_2$, 95% air until the time of injection.

Randomly cycling adult females are mated with vasectomized males to induce a false pregnancy, at the same time as donor females. At the time of embryo transfer, the recipient females are anesthetized and the oviducts are exposed by an incision through the body wall directly over the oviduct. The ovarian bursa is opened and the embryos to be transferred are inserted into the infundibulum. After the transfer, the incision is closed by suturing.

2. Embryonic Stem (ES) Cell Methods

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach,* ed. E. J. Robertson, (IRL Press 1987), the teachings of which are incorporated herein. Selection of the desired clone of transgene-containing ES cells is accomplished through one of several means. In cases involving sequence specific gene integration, a nucleic acid sequence for recombination with the gene or sequences for controlling expression thereof is co-precipitated with a gene encoding a marker such as neomycin resistance. Transfection is carried out by one of several methods described in detail in Lovell-Badge, in *Teratocarcinomas and embryonic stem cells, a practical approach,* ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, a number of ES cells, for example, 0.5× $10^6$, are plated into tissue culture dishes and transfected with a mixture of the linearized nucleic acid sequence and 1 mg of pSV2neo DNA (Southern and Berg, *J. Mol. Appl. Gen.* 1:327–341 (1982)) precipitated in the presence of 50 mg lipofectin in a final volume of 100 μl. The cells are fed with selection medium containing 10% fetal bovine serum in DMEM supplemented with an antibiotic such as G418 (between 200 and 500 μg/ml). Colonies of cells resistant to G418 are isolated using cloning rings and expanded. DNA is extracted from drug resistant clones and Southern blotting experiments using the nucleic acid sequence as a probe are used to identify those clones carrying the desired nucleic acid sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989)). DNA introduction by electroporation is less efficient and requires a selection step. Methods for positive selection of the recombination event (i.e., neo resistance) and dual positive-negative selection (i.e., neo resistance and ganciclovir resistance) and the subsequent identification of the desired clones by PCR have been described by Joyner et al., *Nature* 338, 153–156 (1989) and Capecchi, (1989), the teachings of which are incorporated herein. Naturally cycling or superovulated females mated with males are used to harvest embryos for the injection of ES cells. Embryos of the appropriate age are recovered after successful mating. Embryos are flushed from the uterine horns of mated females and placed in Dulbecco's modified essential medium plus 10% calf serum for injection with ES cells. Approximately 10–20 ES cells are injected into blastocysts using a glass microneedle with an internal diameter of approximately 20 μm.

Randomly cycling adult females are paired with vasectomized males. Recipient females are mated such that they will be at 2.5 to 3.5 days post-mating (for mice, or later for larger animals) when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

3. Identification of Transgenic Animals

Samples (1–2 cm of mouse tails) are removed from young animals. For larger animals, blood or other tissue can be used. To test for chimeras in the homologous recombination experiments, i.e., to look for contribution of the targeted ES cells to the animals, coat color has been used in mice, although blood could be examined in larger animals. DNA is prepared and analyzed by both Southern blot and PCR to detect transgenic founder ($F_0$) animals and their progeny ($F_1$ and $F_2$).

Once the transgenic animals are identified, lines are established by conventional breeding and used as the donors for tissue removal and implantation using standard techniques for implantation into humans.

4. Insertion or Modification of the Genomic DNA

These manipulations are performed by insertion of cDNA or genomic DNA into the embryo using microinjection or other techniques known to those skilled in the art such as electroporation. The DNA is selected on the basis of the purpose for which it is intended: to inactivate a gene, for example, a gene encoding an enzyme. The enzyme encoding gene can be modified by homologous recombination with a DNA for a defective enzyme, such as one containing within the coding sequence an antibiotic marker, which can then be used for selection purposes.

C. Analysis of Transgenic Animals.

Originally one founder mouse was identified by Southern blotting of BamHI fragmented tail genomic DNA probed with a CMV promoter probe. The CMV promoter probe allows clean Southern blotting results since mice do not naturally contain CMV sequences. The founder mouse exhibited three BamHI fragments hybridizing to the CMV promoter probe. The founder mouse was bred to non-transgenic mice and DNA from the resulting offspring were subjected to Southern blot analysis. These mice displayed either one of the original BamHI fragments (the A pattern) or the other two BamHI fragments (the B pattern). From this it could be concluded that the syndecan construct was inserted at two independently segregating locations in the genome of the founder mouse. The A insert has a single copy of the syndecan construct inserted (this was confirmed by isolation of the entire insertion region). The B insertion contains at least two copies of the syndecan construct inserted at one location.

Syndecan-1 expressing mice containing either construct exhibit an obese phenotype in adulthood, with mice containing the A insertion exhibiting greater obesity. It was determined that the A insertion does not insertionally inactivate any of the genes known to affect weight in mice. This, along with the location-independent obesity phenotype seen for both insertion sites, confirms that expression of the syndecan construct, rather than insertional mutagenesis is the likely cause of the obesity phenotype. It was also determined that the pattern of expression of syndecan-1 in mice containing the two constructs was the same, although the B construct expressed syndecan-1 at a lower level than the A construct. Significantly, mice containing the A construct exhibit more profound obesity than mice containing the B construct.

The tables demonstrate that obesity increases with age and onset of maturity, and is correlated with genotype. Body weights and tail lengths of male and female mice were measured beginning at 10 days. Values are the mean±SEM. Data for males are from A, C, E, F and G lines, while data for females are from A, B, C, F and G lines: A, B, and E lines contain the identical syndecan-1 construct; the construct in the C, F and G lines was mutated by inserting three stop codons following the signal peptide, preventing translation. By 24 weeks of age transgenic line A homozygotes weighed an average of 52±4 g (n=6) in females (p<0.0001) and 61±2 g (n=5) in males (p<0.0001), hemizygotes showed an intermediate weight gain averaging 37±2 g (n=14) in females (p<0.0001) and 49±2 g (n=13) in males (p<0.0001). Control FVB and non-translatable transgenic mice (lines C, F, and G) weighed an average of 21±1 g (n=7) in females and 31±1 g (n+5) in males at 24 weeks of age. Weight difference in syndecan-1 overexpression mice is detectable by 7 weeks of age. Weight difference in syndecan-1 overexpression mice is detectable by 7 weeks with A line homozygote males weighing 33.4±2.6 g (p<0.05) and females 24.2±0.9 g (p<0.05), while control males weigh 25.2±1.4 g and females 21.0±1.1 g. Tail length showed no significance difference between any of the transgenic lines, indicating that their linear rate of growth was similar.

Body length was measured from the tip of the nose to the anus in 6 month old mice. A/A line mice are larger than their control by approximately 1 cm similar to observations made in the agouti/MC4R obese mice.

Food consumption in A/A and control +/+ mice at 6 weeks and 6 months of age was compared. Food consumption was monitored daily for two weeks in female and male mice at six weeks and six months of age. Both male and female A/A line mice consume more food than their control littermates and the hyperphagia increases with increased age and body weight.

Table 1 demonstrates the effect of the syndecan-1 on triglyceride levels. Results indicate that there is small increase in plasma triglyceride level in A line mice. Table 1 is an analysis of total carcass triglyceride in syndecan-1 A line mice. Syndecan-1 overexpression mice accumulated fat in all adipose tissue depots visualized by magnetic resonance imaging. Amount of fat varied between different genotypes and correlated with the obesity of the mice. Homozygote A male mice contained 3.6-fold more triglyceride than their controls while females contained 4.7-fold more triglyceride.

TABLE 1

Carcass triglyceride analysis of syndecan-1 overexpression mice

| Genotype (sex) | Weight (g) | Triglyceride (g) |
| --- | --- | --- |
| +/+ (male) | 30.2 ± 1.9 | 4.7 ± 0.6 |
| A/A (male) | 48.3 ± 2.0 | 17.0 ± 1.5 |
| +/+ (female) | 27.1 ± 2.4 | 4.6 ± 0.7 |
| A/A (female) | 56.6 ± 3.3 | 21.9 ± 0.2 | mean ± SEM, n = 4
age: males 5 months old
females 8 months old
p < 0.005 between +/+ and A/A mice.

Plasma leptin levels in syndecan-1 A line mice were analyzed from plasma of pre-obese (six weeks) and obese (six month) male and mice by radioimmunoassay using a mouse leptin standard. As the mice become overtly obese, plasma levels of leptin elevate correlating with their weight. Prior to the onset of obesity, plasma levels of leptin are not significantly elevated when compared to control (+/+) mice.

Plasma insulin levels in syndecan-1 A line mice were analyzed from plasma of pre-obese (six weeks) and obese (six month) male and female mice by radioimmunoassay using a rat insulin standard. Plasma insulin levels are elevated only with the most severe obesity seen predominantly in the males. Prior to the onset of obesity, plasma levels of insulin are not significantly elevated when compared to control (+/+) mice.

Plasma glucose levels were assayed from plasma of control (+/+), heterozygote (A/+), and homozygote (A/A) mice. The level of plasma glucose is elevated only with severe obesity seen predominantly in the males.

No significant increase in corticosterone levels were observed in the syndecan-1 A line mice, which is similar to what has been observed in the agouti/MC4R obese mice and in marked contrast to levels observed in the db and ob obese mice.

Plasma levels of the soluble syndecan-1 ectodomain in overexpression mice was detected only in lines A, B and E. Wildtype and nontranslatable mutant lines (C, F and G) showed no detectable syndecan-1.

These results are summarized in Table 2 for syndecan-1 A line mice, comparing plasma glucose, insulin, leptin and corticosterone in syndecan-1 A line and control (+/+) mice measured at 6 weeks and 6 months.

TABLE 2

Plasma constituents in syndecan-1 A line mice

| | Glucose (mg/dl) | Insulin (ng/ml) | Leptin (ng/ml) | Corticosterone (ng/ml) |
|---|---|---|---|---|
| 6 week males | | | | |
| +/+ (n = 5) | 204 ± 21 | 1.2 ± 0.1 | 2.8 ± 0.8 | n.d. |
| A/A (n = 5) | 250 ± 45 | 1.2 ± 0.4 | 3.2 ± 0.5 | n.d. |
| 6 week females | | | | |
| +/+ (n = 5) | 180 ± 25 | 1.5 ± 0.5 | 1.9 ± 0.4 | n.d |
| A/A (n = 5) | 190 ± 50 | 1.9 ± 0.4 | 1.8 ± 0.2 | n.d. |
| 6 mos. males | | | | |
| +/+ (n = 6) | 176 ± 25* | 1.1 ± 0.2‡ | 3.1 ± 0.2* | 16.5 ± 3.0 |
| A/A (n = 5) | 508 ± 16* | 64.3 ± 19‡ | 17.0 ± 1.2* | 20.0 ± 0.7 |
| 6 mos females | | | | |
| +/+ (n = 7) | 126 ± 5† | 0.4 ± 0.2† | 2.5 ± 0.5‡ | 29 ± 8.0 |
| A/A (n = 6) | 248 ± 54† | 9.4 ± 3.0† | 28.4 ± 5.5‡ | 30 ± 8.0 | n.d. = not determine
† = $p < 0.05$
‡ = $p < 0.005$
* = $p < 0.0001$

As shown above, leptin levels correlate with obesity, hyperinsulinemia and hyperglycermia are markedly pronounced in the obese (6 months) males, while corticosterone is not elevated.

Expression analysis was performed using monoclonal 281-2 by immunohistochemical analysis of tissues. The results are shown in Table 3. Unless otherwise noted staining was observed along the cell surface. * indicates intracellular localization.

bladder, the level of expression the transgenic A and B line tissues was much greater than the controls (+/+). Syndecan-1 was not detected in the brain, heart, kidney, pancreas, skeletal muscle, and adrenal gland of control mice.

Immunohistochemical and in situ hybridization analyses of syndecan-1 expression in the hypothalamic regions of syndecan-1 A/A, B/+, C/C, and control mice show that the transgene is expressed in similar nuclei of the hypothalamus indicating that transgene expression is independent of the phenotype. Thus elements in the transgene are sufficient to drive expression in the brain. Expression was observed in the paraventricular, suprachiasmatic, lateral, dorso-medial, and arcuate nuclei of the hypothalamus. Syndecan-1 transgene is expressed in the hypothalamus regions that regulate energy balance.

In summary, "syndtrophin" ("syndein" Greek for "to bind together"; "trophus" Greek for "round and well nourished") mice are similar to obese humans. They exhibit normal development, growth and fertility. The results demonstrate that, prior to obesity, food intake is excessive, blood levels of soluble ectodomain are elevated, and the syndecan misexpression is localized in hypothalamic regions that control energy balance. Onset of obesity occurs after sexual maturity and affects all adipose tissue sites.

TABLE 3

Localization of syndecan-1 in +/+ and A/A mice.

| Tissue | Expression level | Cell Type | Tissue | Expression level | Cell type |
|---|---|---|---|---|---|
| Heart | − | not detected | Heart | +++ | cardiac muscle cell* |
| Kidney | − | not detected | Kidney | +++ | kidney tubule |
| Pancreas | − | not detected | Pancreas | +++ | acinus, islets of Langerhans |
| Skeletal Muscle | − | not detected | Skeletal Muscle | +++ | muscle cell* |
| Adrenal gland | − | not detected | Adrenal gland | ++ | medulla |
| Skin | +++ | epidermis | Skin | +++ | epidermis |
| Lung | + | type II cell? | Lung | + | type II cell? |
| Spleen | + | white pulp, ? cell | Spleen | + | white pulp, ? cell |
| Liver | + | sinusoid, endothelial cell | Liver | + | sinusoid, endothelial cell? |
| Thyroid | − | not detected | Thyroid | − | not detected |
| Testes | + | epithelial cell | Testes | + | epithelial cell |
| Epididymis | + | epithelial cell | Epididymis | + | epithelial cell |
| Seminal Vesicles | + | epithelial cell | Seminal Vesicles | ++ | epithelial cell |
| Fat | − | not detected | Fat | − | not detected |
| Bladder | +++ | epithelial cell | Bladder | +++ | epithelial cell |

Table 3 shows tissues which express syndecan-1 in the overexpression mice. With the exception of skin and

TABLE 4

Characteristics of mouse obesity syndromes

| Mouse mutant | Inheritance | obesity onset | elevated leptin | elevated insulin | hyperglycemia | elevated corticosterone | increased body size | hyperphagia |
|---|---|---|---|---|---|---|---|---|
| ob/ob | recessive | early | n/a | @ 4 weeks | strain dependent | yes | no | high |
| db/db | recessive | early | yes | @ 10 days | strain dependent | yes | no | high |
| agouti | dominant | adult | yes | male > females | males | no | yes | mild |

TABLE 4-continued

Characteristics of mouse obesity syndromes

| Mouse mutant | Inheritance | obesity onset | elevated leptin | elevated insulin | hyperglycemia | elevated corticosterone | increased body size | hyperphagia |
|---|---|---|---|---|---|---|---|---|
| mc4R-ko | semi-dominant | adult | yes | @ 2 mos males > females @ 2 mos | only males only | no | yes | mild |
| FVB/N-TgN | dominant | adult | yes | males > females @ 6 mos | males only | no | yes | high in old mild in 6 (synd-1)aMB weeks |

Table 4 is a comparison of mouse obesity syndromes. This comparison attempts to illustrate the similarities and differences between the obese mouse mutants and the syndecan-1 obese mouse. It is clear that the syndecan-1 mouse is quite similar physiologically to the agouti/MC4R obese mice. It is likely that the syndecan-1 protein impinges either directly or indirectly on the agouti/MC4R signaling cascade.

II. Development of Weight Regulating Compounds

Heparan sulfate proteoglycans (HSPGs) alter the activity of many proteins, including extracellular matrix (ECM) components, growth factors, antiproteases, and lipases. Syndecans can bind extracellular molecules as receptors or as co-receptors and/or signal transducing receptors, for example, as receptors (e.g., lipoprotein lipase internalization), or co-receptors for the action of growth factors (e.g., FGF signaling) and extracellular matrix components (e.g., adhesion to fibronectin with actin cytoskeleton reorganization). The syndecan family of transmembrane PGs includes most of the HS at cell surfaces but these PGs may also be shed, becoming paracrine effectors. The syndecan ectodomain can be cleaved near the plasma membrane and released into the extracellular milieu as a soluble proteoglycan. The shed syndecan can activate or inhibit the action of its ligands on adjacent cells, thus acting as a paracrine effector. The heparan sulfate chains may be partially degraded by extracellular heparanases at inflammatory sites, releasing oligosaccharides that can act as mediators.

It is significant that the transgene is ectopically expressed in the brain, in the hypothalamic centers that regulate body weight but in no other brain sites. Specifically, the arcuate, paraventricular, dorsomedial and lateral hypothalamic nuclei express both the transgene mRNA and syndecan-1. This misexpression increases as the mice develop post-natally. In contrast, normal mice have no or very low levels of expression of syndecan-1 and syndecan-3, respectively, in the post-natal brain.

Understanding the mechanism of action of these animals' weight gains and having the animals to test potential treatments makes available means both for increasing appetite as well as suppressing appetite, and concordant weight gain. This not only has medical applications but may be of use in agriculture, where animals can be treated with a compound which mimics a syndecan and which can pass through the blood brain barrier. These compounds should act in a manner analogous to the growth factors currently in wide usage.

These mice show that syndecan-1 is shed and that HSPGs can alter energy balance, providing a genetic model for maturity onset obesity that resembles the human condition. The phenotype mimics the human condition in several respects. The obesity begins only after sexual maturity, fat accumulates in all adipose tissue depots, the mice eat excessively and are less active physically, but otherwise show no abnormalities, including normal fertility in heterozygotes. Thus, these mice become fat by the same route that most people do: they eat too much. Blood levels of the hormones leptin and insulin are elevated and correlate with body fat, but only the most obese males are diabetic. The normal syndecan-1 gene is expressed at the cell surfaces of many tissues but not in the post-natal brain. The transgene is expressed in most tissues and blood levels of the soluble syndecan-1 extracellular domain are markedly elevated in these mice. It is significant that these high blood levels precede the onset of obesity.

III. Interaction of Syndecan with Hypothalamic Neuropetide Regulation of Body Weight A. Interaction of Syndecan with Neuropeptides.

1. Binding of Syndecan to Neuropeptides

Binding of syndecan-1 ectodomain to neuropeptides involved in body weight regulation was tested. Varying concentrations of the peptides were immobilized on a nitrocellulose membrane (for example, 1000 nmol) and fixed by UV cross-linking. The membrane was incubated with radioactive syndecan-1 ectodomain to allow binding and then washed and analyzed by autoradiography.

Only fibroblast growth factor-2 (FGF-2), vasopressin, Agouti-related protein (AGRP) and agouti of the various neuropeptides tested interact with syndecan-1. Of these, only AGRP and agouti of these have been extensively physiologically characterized and shown to regulate feeding behaviour. AGRP is the hypothalamic analog of agouti. Agouti is a paracrine signaling molecule that induces hair follicle melanocytes to switch from the synthesis of black pigment to yellow pigment. Mice expressing the agouti gene are obese and more susceptible to tumor formation. Yen, et al., *FASEB J.* 8, 479–488 (1994). Recombinant Agouti-related protein is a potent, selective antagonist of Mc3r and Mc4r, melanocortin receptor subtypes. (Ollmann, et al., *Science* 278, 135–138 (October 1997). The MC4-R is a seven pass transmembrane receptor that activates a G-protein (G_) and stimulates adenylyl cyclase leading to the generation of cAMP. Activation of the receptor is achieved via binding of melanocortin peptides, specifically þMSH. The receptor may be inhibited by the peptides agouti and agouti related protein (AGRP). This receptor is normally expressed in the brain including the lateral area of the hypothalamus regions that also express syndecan-1 in syndtrophin mice.

The agouti and agouti-related protein (AGRP):

|  | Agouti | Agouti-related protein (AGRP) |
|---|---|---|
| size (aa) | 131 | 132 |
| Localization | skin, testes | hypothalamus, adrenal |
| þMSH Competitive Inhibitor | MC1-R MC2-R MC4-R | MC3-R MC4-R |
| Function | Melanocyte >Convert eumelanin To pheomelanin | Hypothalamus >anti-satiety factor |
| ectopic expression | agouti mutation >obese >Yellow coat | AGRP transgenic >obese |

2. Functional Interaction between Syndecan and AGRP

Based on the interaction of AGRP and syndecan-1, the putative interaction between agouti/AGRP and syndecani-heparan sulfate in a functional assay was tested. Membranes from 293 cells transfected with the melanocortin-4 receptor were preincubated with buffer or as indicated with AGRP, heparan sulfate, syndecan-1 ectodomain, heparan sulfate plus AGRP, and syndecan-1 ectodomain plus AGRP. Samples were then mixed with or without the indicated concentration of ndp-þMSH and conversion of ATP to cAMP measured in the assay.

Figure 1A:
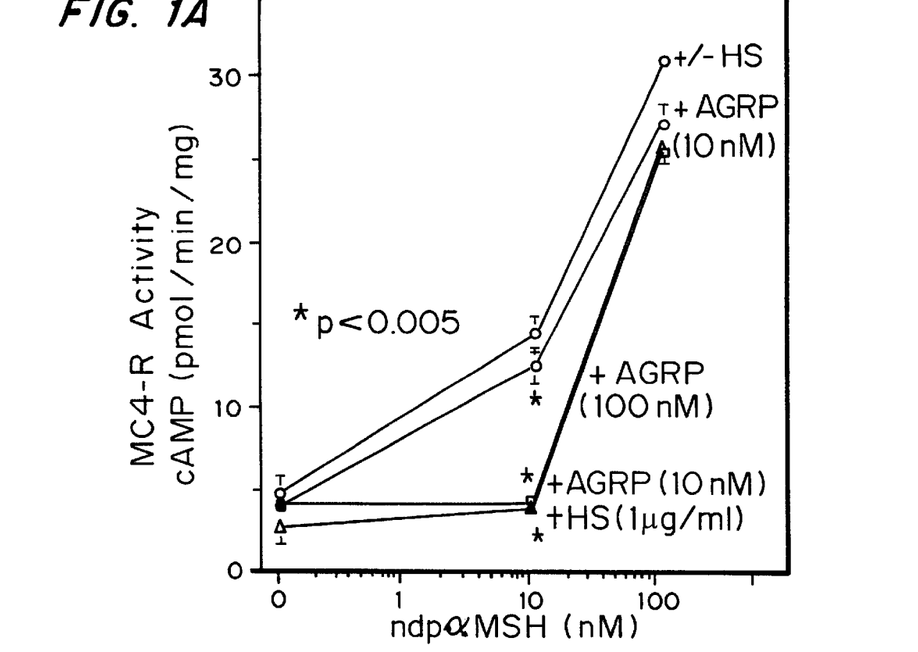
FIGS. 1a and 1b are graphs showing that heparan sulfate or syndecan-1 ectodomain potentiates melanocortin-4R (MC4-R) inhibition by AGRP. Membranes from 293 cells transfected with the melanocortin-4 receptor were preincubated with buffer or with AGRP, heparan sulfate, syndecan-1 ectodomain (0, 1, 10, and 100 ng/ml), heparan sulfate plus AGRP (10 nM, 100 nM, or 1 micromolar), and syndecan-1 ectodomain plus AGRP. Samples were then mixed with or without the indicated concentration of ndp-þMSH (0, 10 or 100 nM) and conversion of ATP to cAMP measured (cAMP, pmol/min/mg) in a standard assay as a function of MC4-R activity (FIG. 1a, plotting MC4-R activity as a function of ndp-þMSH concentration.
Figure 1B:
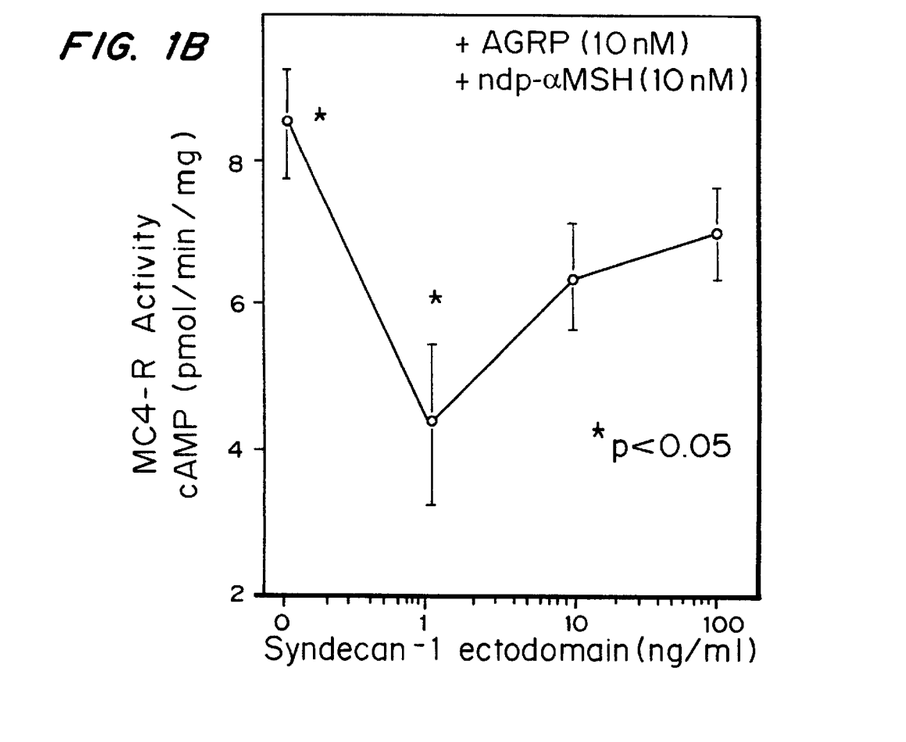

FIGS. 1a and 1b are graphs showing that heparan sulfate or syndecan-1 ectodomain potentiates melanocortin-4R (MC4-R) inhibition by AGRP. This assay shows that the syndecan-1 ectodomain as well as heparan sulfate can potentiate the inhibitory action of AGRP on the MC4-R activity as measured by the formation of cAMP from ATP. In the presence of 1 ng/ml syndecan-1 ectodomain or 1 µg/ml heparan sulfate, 10 nM AGRP is as potent as 100 nM AGRP at inhibiting MC4-R activation. However, the kinetics of the interaction are complex since low concentrations of syndecan-1 ectodomain potentiates AGRP's action and the potentiation is less pronounced at higher concentrations.

3. Genetic Studies with Syndecan in Agouti Mice

Figure 2:
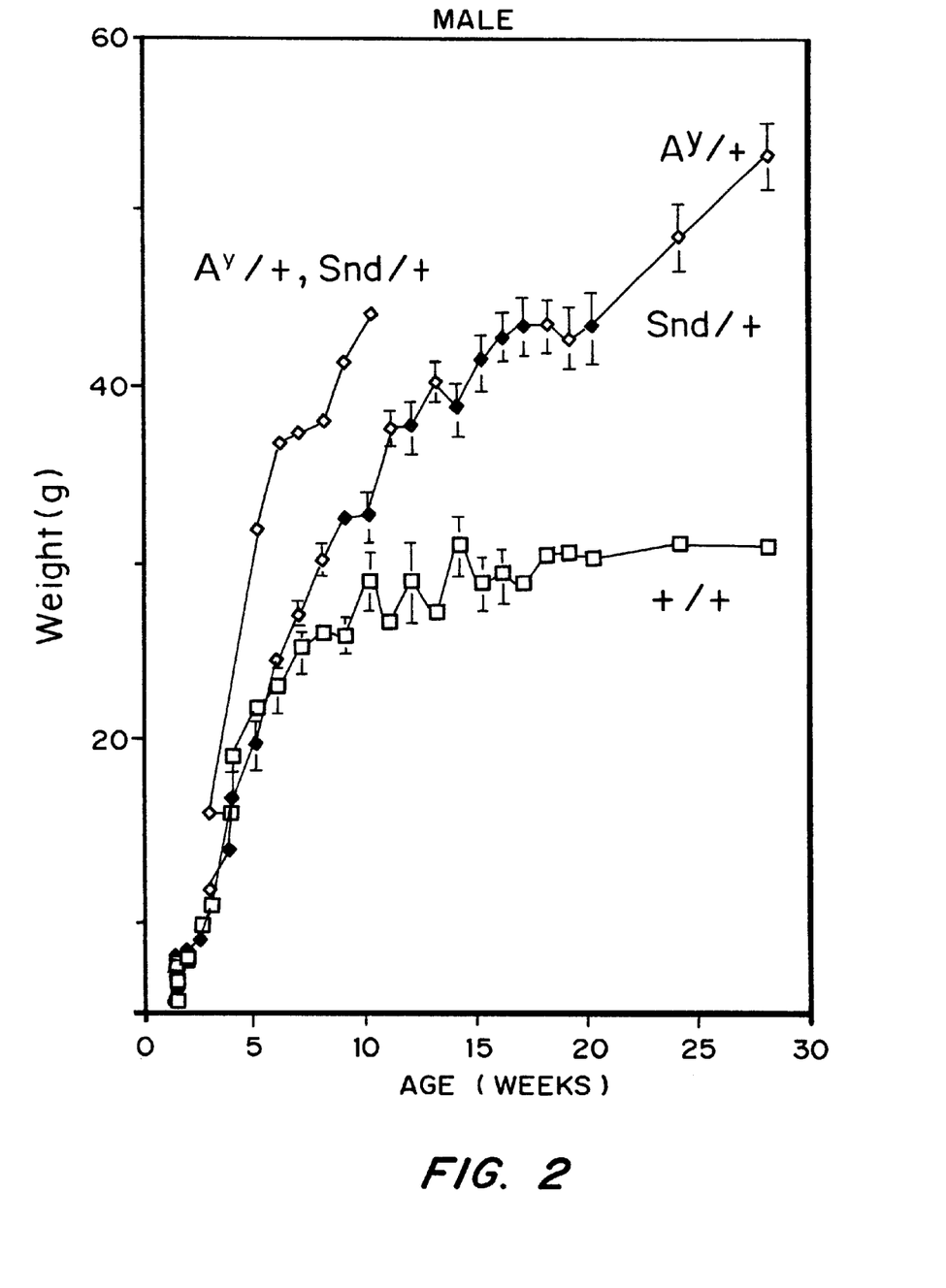
FIG. 2 is a graph (weight, g, versus age, weeks) showing that the genetic interaction between syndtrophin (Snd/+) and agouti ($A^y$) mice potentiates obesity. Graph is based on a single animal of genotype $A^y$/+x Snd/+ observed for 12 weeks.

Genetic studies were then conduction to examine the genetic interaction between syndtrophin and agouti ($A^y$) mice. The results, shown in FIG. 2, demonstrate that the combination potentiates obesity. The data provide physiological evidence for an interaction between agouti and syndecan-1. The double heterozygote ($A^y$/+ x Snd/+) shows both earlier onset of obesity and the extent of the obesity is greater than the sum of the individual weights of $A^y$ and syndtrophin mice. Since syndecan-1 potentiates the action of agouti on the MC4-R in a similar manner as its action on AGRP in the biochemical assay, it is likely that in the hypothalamus of these double heterozygotes there is a physiological interaction which leads to the potentiation of the obesity.

B. Role of Syndecan in Hypothalamic Neuropeptide Regulation of Body Weight.

Figure 3:
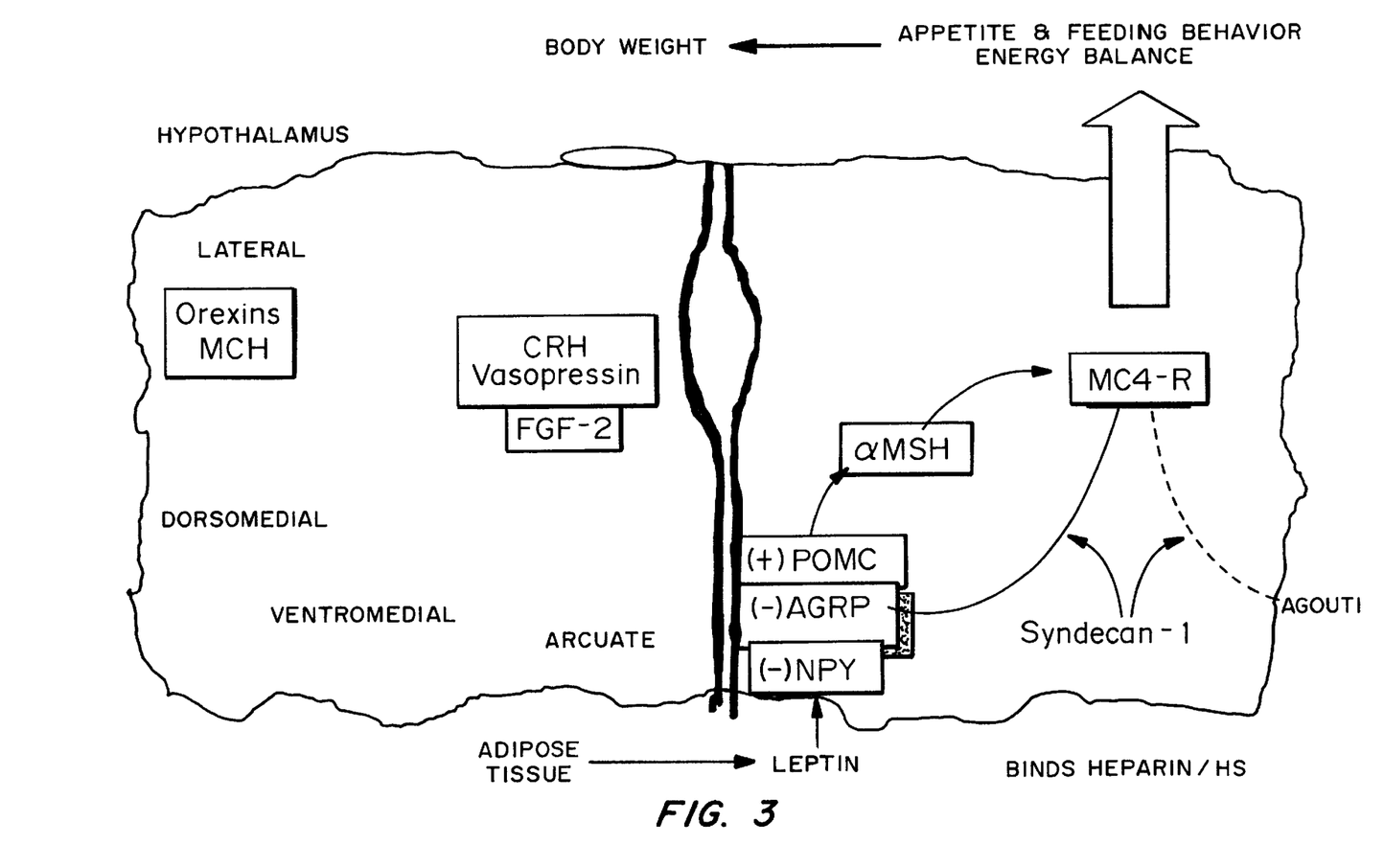
FIG. 3 is a schematic showing hypothalamic neuropeptide regulation of body weight and the putative role of syndecan-1 in the physiology of body weight regulation.

FIG. 3 is a schematic of the presumed interaction of syndecan-1 with the MC4-R pathway relating to regulation of body weight. Syndecan-1 is believed to bind to the MC4-R, potentiating its effect on appetite and feeding behavior, downstream of leptin's effect on MC4-R.

It should be understood that while the studies described above utilize syndecan-1, it will be apparent to those skilled in the art of syndecans that other syndecans -2, -3, and -4 which constitute the syndecan family (referred to herein merely as "syndecans") and proteoglycan molecules such as glypican could be substituted for syndecan-1.

IV. Design and Testing of Compounds Regulating Body Weight

Based on these findings, compounds can be designed and tested which will either enhance or reduce appetite and activity. These are then useful as treatments for a wide range of eating disorders, including idiopathic obesity, anorexia nervosa, and cachexia due to disease, for example, cancer, cancer chemotherapy, chronic inflammatory diseases, rheumatoid and collagen diseases and chronic infections.

The data show that syndecan-1 ectodomain is able to bind to and potentiate the inhibitory action of AGRP at the melanocortin-4 receptor. Since heparan sulfate is also able to potentiate this inhibitory activity, it is expected that there are brain specific heparan sulfate proteoglycans which are mediating AGRP's activity. Therefore, a rational therapeutic target is to design molecule(s) which interfere with the interaction between heparan sulfate proteoglycans and AGRP. Based on the available data, it is expected that the interacting domain on AGRP is within its amino terminal region. The carboxyl terminal domain likely interacts with the melanocortin-4 receptor and inhibits the binding of þMSH.

A competitive binding assay could be set up to identify potential molecules which interfere with the heparan sulfate proteoglycan-AGRP interaction. Specifically, the assay is designed to identify molecules which interfere with the interaction between the amino terminal domain of AGRP and heparan sulfate proteoglycans. Molecules identified in this assay are then tested for their ability to inhibit AGRP action in a functional assay, e.g. measuring activation of adenylyl cyclase in response to þMSH. These molecules are then tested syndtrophin and agouti ($A^y$) mice as well as other models such as db/db and ob/ob, to determine their efficacy in divergent obesity syndromes.

These compounds are basically grouped as follows:

A. Regulators of feeding behavior.

Agents that mimic or destroy or modify syndecan can act as agonists or antagonists, inhibiting a satiety factor or stimulating a feeding factor. These agents can be similar to the intact proteoglycan, the glycosaminoglycan chains such as heparan sulfate or chondroitin sulfate, the core protein, or oligosaccharides, organic glycomimetics, or enzymes that degrade the glycosaminoglycan chains.

B. Regulators of syndecan expression.

Agents that turn on syndecan expression will have the same effects as the syndecan mimicking agents. An example is the antibacterial peptides referred to as synducin, PR-39, described in PCT/US95/12080 "Synducin Mediated Modulation of Tissue Repair" by Children's Medical Center Corporation. Another example would be the oligonucleotides now in use which inhibit expression, for example, antisense, ribozymes, or external guide sequences for RNAase P.

C. Targeting specific brain regions.

A DNA construct that results in expression of the syndecan transgene in those areas of the hypothalamus responsible for the regulation of body weight and energy balance. The construct described herein must include a transcriptional activator specific for that region of the brain, since inserts at two segregating loci both produced the same phenotype. Additionally, a control construct (lines C, F and G) also express transgene mRNA in these hypothalmic centers. The transcriptional activator sequence can therefore also be a target to increase or decrease expression in the hypothalamus of syndecan or other known genes involved in weight regulation.

D. Hormonal regulators.

It is apparent from the data that hormones play a role in syndecan expression and obesity in mature animals.

Accordingly, one could also alter the pathway in which the hormones expressed as a result of the syndecan expression in the hypothalamus are regulated.

The compounds described above can be designed based on information already known to those skilled in the art, such as the DNA sequence encoding the syndecans, the protein and carbohydrate structures of the syndecans and other proteoglycans, and then routinely screened using the transgenic mice described herein or mice developed in a similar way. Useful compounds are designed based on methods known to those skilled in the art. The criteria for assessing response to therapeutic modalities employing these compounds is dictated by the specific condition and will generally follow standard medical practices.

Random Generation of Binding Molecules

Molecules with a given function, catalytic or ligand-binding, can be selected for from a complex mixture of random molecules in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992).

Computer Assisted Drug Design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159–166; Ripka, *New Scientist* 54–57 (Jun. 16, 1988); McKinaly and Rossman, 1989 *Annu. Rev. Pharmacol. Toxicol.* 29, 111–122; Perry and Davies, *QSAR: Quantitative Structure-Activity Relationships in Drug Design* pp. 189–193 (Alan R. Liss, inc. 1989); Lewis and Dean, 1989 *Proc. R. Soc. Lond.* 236, 125–140 and 141–162; and, with respect to a model receptor for nucleic acid components, Askew, et al., 1989 *J. Am. Chem. Soc.* 111, 1082–1090. Other computer programs that screen and graphically depict chemicals are available from companies such as BioDesign, Inc., Pasadena, Calif., Allelix, Inc., Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators of syndecan expression.

Nucleotide molecules which bind either syndecan, syndecan components or genes regulating expression of or encoding syndecan can be generated in vitro, and then inserted into cells. Oligonucleotides can be synthesized on an automated synthesizer (e.g., Model 8700 automated synthesizer of Milligen-Biosearch, Burlington, Mass. or ABI Model 380B). (see, e.g., Offensperger et al., 1993 *EMBO J.* 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079–7083 (synthesis of antisense oligonucleoside phosphoramidates and phosphorothioates to inhibit replication of human immunodeficiency virus-1); Sarin et al., 1989 *Proc. Natl. Acad. Sci. USA* 85, 7448–7794 (synthesis of antisense methylphosphonate oligonucleotides); Shaw et al., 1991 *Nucleic Acids Res* 19, 747–750 (synthesis of 3' exonuclease-resistant oligonucleotides containing 3' terminal phosphoroamidate modifications); incorporated herein by reference). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., 1992).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., in *Ann. Rev. Biochem.* 1984 53, 323–356 (phosphotriester and phosphite-triester methods); Narang et al., in *Methods Enzymol.,* 65, 610–620 (1980) (phosphotriester method).

Preparation of Peptides

Proteins can be expressed recombinantly and cleaved by enzymatic digest, expressed from a sequence encoding a peptide, or synthesized using standard techniques. It is a routine matter to make appropriate peptides, test for binding or inhibition, and then utilize. The peptides can be as short as twenty six amino acids in length and up to 57 amino acids, and are easily prepared by standard techniques. They can also be modified to increase in vivo half-life, by chemical modification of the amino acids or by attachment to a carrier molecule or inert substrate.

The peptides can also be conjugated to a carrier protein such as keyhole limpet hemocyanin by its N-terminal cysteine by standard procedures such as the commercial Imject kit from Pierce Chemicals or expressed as a fusion protein, which may have increased efficacy. These methods are known to those skilled in the art. An example is the solid phase synthesis described by J. Merrifield, 1964 *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having identical sequence to the receptor proteins described herein, or substitutions or additions of amino acids, which can be screened for activity as described above.

The peptide can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

Carbohydrate Reagents

Carbohydrate components (the O-glycan structures or components thereof) of the ligand or the antibodies, in an appropriate pharmaceutical carrier, can be administered intramuscularly, intraperitoneally, subcutaneously, orally, as the carbohydrate, conjugated to a carrier molecule, or in a drug delivery device. The carbohydrate can be modified chemically to increase its in vivo half-life.

The carbohydrate can be isolated from cells expressing the carbohydrate, either naturally or as a result of genetic engineering as described in the transfected mammalian cell examples, or, preferably, by synthetic means. These methods are known to those skilled in the art. In addition, a large number of additional glycosyltransferases have been cloned (J. C. Paulson and K. J. Colley, J. Biol. Chem. 264:17615–17618, 1989). Accordingly, workers skilled in the art can use a combination of synthetic chemistry and enzymatic synthesis to make pharmaceuticals or diagnostic reagents.

Antibodies

In vivo Immunization of Animals

Animals such as mice may be immunized by administration of an amount of immunogen effective to produce an immune response. Preferably a mouse is subcutaneously injected in the back with 100 micrograms of antigen, followed three weeks later with an intraperitoneal injection of 100 micrograms of immunogen with adjuvant, most preferably Freund's complete adjuvant. Additional intraperitoneal injections every two weeks with adjuvant, preferably Freund's incomplete adjuvant, may be necessary until the property titer in the mouse's blood is achieved. In order to use the mice for fusion and hybridoma production, a titer of at least 1:5000 is preferred, and a titer of 1:100,000 or more is most preferred.

In vitro Immunization

The technique of in vitro immunization of human lymphocytes is frequently employed to generate a large variety of human monoclonal antibodies, since deliberate in vivo priming of humans with many antigens of interest is not feasible until approval by the Food and Drug Administration has been obtained. Techniques for in vitro immunization of human lymphocytes are well known to those skilled in the art. See, e.g., T. Inai, et al., *Histochemistry* (German), 99(5):335–362 (May 1993); A. Mulder, et al., *Hum. Immunol.*, 36(3):186–192 (March 1993); H. Harada, et al.,*J. Oral Pathol. Med.* (Denmark), 22(f):145–152 (April 1993); N. Stauber, et al., *J. Immunol. Methods* (Netherlands), 161(2):157–168 (May 26, 1993); and S. Venkateswaran, et al., *Hybridoma,* 11(6)729–739 (December 1992), which are incorporated herein by reference. These techniques can be used to produce antigen-reactive human monoclonal antibodies, including antigen-specific IgG, and IgM human monoclonal antibodies.

Humanization of Antibodies

Because the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarity-determining hypervariable regions (CDRs) are of non-human origin, whereas all framework regions (FR) of variable domains are products of human genes. These "humanized" antibodies present a less xenograft-like rejection stimulus when introduced to a human recipient.

To accomplish humanization of a selected mouse monoclonal antibody, the CDR grafting method described by Daugherty, et al., *Nucl. Acids Res.,* 19:2471–2476 (1991), incorporated herein by reference, may be used. Briefly, the variable region DNA of a selected animal recombinant anti-idiotypic ScFv is sequenced by the method of Clackson, T., et al., *Nature,* 352:624–688, 1991, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md. 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

Pharmaceutical Compositions

The compounds described above are preferably administered in a pharmaceutically acceptable vehicle. Suitable pharmaceutical vehicles are known to those skilled in the art. Suitable pharmaceutical vehicles for administration to a patient are known to those skilled in the art. For parenteral administration, the carbohydrate will usually be dissolved or suspended in sterile water or saline. For enteral administration, the carbohydrate will be incorporated into an inert carrier in tablet, liquid, or capsular form. Suitable carriers may be starches or sugars and include lubricants, flavorings, binders, and other materials of the same nature. The carbohydrate can also be administered locally at a wound or inflammatory site by topical application of a solution or cream.

Alternatively, the carbohydrate may be administered in, on or as part of, liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", Drug Carriers in Biology and Medicine pp. 287–341 (Academic Press, 1979). Microspheres formed of polymers or proteins are well known to those skilled in the art, and can be tailored for passage through the gastrointestinal tract directly into the bloodstream. Alternatively, the carbohydrate can be incorporated and the microspheres, or composite of microspheres, implanted for slow release over a period of time, ranging from days to months. See, for example, U.S. Pat. Nos. 4,906,474, 4,925,673, and 3,625,214. The compounds can also be administered locally by topical application of a solution, cream, gel, or polymeric material (for example, a Pluronic™, BASF).

Modifications and variations of these methods for designing, testing, and using compounds for regulation of body weight, will be obvious to those skilled in the art from the foregoing detailed description and are intended to come within the scope of the appended claims.

We claim:

1. A method for regulating body weight comprising administering to an animal a compound which interfers with the interaction between heparan sulfate proteoglycans and Agouti-related protein ("AGRP").

2. The method of claim 1 wherein the compound interferes with melanocortin 4 receptor function mediated by interaction with syndecan.

3. The method of claim 1 wherein the compound is a syndecan or a mimic thereof of its binding ability.

4. The method of claim 1 wherein the compound interferes with interactions involving the amino terminal region of AGRP.

5. The method of claim 1 wherein the compound binds to the carboxyl terminal domain of AGRP.

6. The method of claim 1 wherein the compound competitively inhibits the heparan sulfate proteoglycan-AGRP interaction.

7. The method of claim 1 wherein the compound can pass the blood brain barrier.

8. The method of claim 1 wherein the compound is administered by genetically engineering the animal to express a compound modulating binding to melanocortin 4 receptor.

9. The method of claim 1 wherein the compound is administered as a pharmaceutically acceptable composition.

10. The method of claim 1 wherein the animal has a wasting disorder.

11. The method of claim 10 wherein the disorder is selected from the group consisting of idiopathic obesity, anorexia nervosa, and chachexia due to disease.

12. The method of claim 11 wherein the disorder is chachexia due to a disease selected from the group consisting of cancer, cancer chemotherapy, chronic inflammatory diseases, rheumatoid and collagen diseases and chronic infections.

* * * * *